(12) United States Patent
Akamatsu et al.

(10) Patent No.: US 9,399,759 B2
(45) Date of Patent: Jul. 26, 2016

(54) METHOD FOR PRODUCING NEUROSPHERES

(75) Inventors: Wado Akamatsu, Tokyo (JP); Hideyuki Okano, Tokyo (JP)

(73) Assignee: Keio University, Minato-ku, Tokyo (JP)

( * ) Notice: Subject to any disclaimer, the term of this patent is extended or adjusted under 35 U.S.C. 154(b) by 628 days.

(21) Appl. No.: 13/127,566

(22) PCT Filed: Nov. 4, 2009

(86) PCT No.: PCT/JP2009/005856
§ 371 (c)(1),
(2), (4) Date: Jun. 16, 2011

(87) PCT Pub. No.: WO2010/052904
PCT Pub. Date: May 14, 2010

(65) Prior Publication Data
US 2011/0250684 A1    Oct. 13, 2011

Related U.S. Application Data

(60) Provisional application No. 61/198,365, filed on Nov. 5, 2008.

(51) Int. Cl.
*C12N 5/0797*    (2010.01)
(52) U.S. Cl.
CPC .......... *C12N 5/0623* (2013.01); *C12N 2500/25* (2013.01); *C12N 2500/46* (2013.01); *C12N 2501/01* (2013.01); *C12N 2501/115* (2013.01); *C12N 2501/235* (2013.01); *C12N 2501/602* (2013.01); *C12N 2501/603* (2013.01); *C12N 2501/604* (2013.01); *C12N 2501/606* (2013.01); *C12N 2506/13* (2013.01); *C12N 2506/1307* (2013.01)

(58) Field of Classification Search
CPC ............. C12N 5/0623; C12N 2500/25; C12N 2500/46; C12N 2501/01; C12N 2501/115; C12N 2501/235; C12N 2501/602; C12N 2501/603; C12N 2501/604; C12N 2501/606; C12N 2506/13; C12N 2506/1307
See application file for complete search history.

(56) References Cited

U.S. PATENT DOCUMENTS

| 2004/0092012 | A1 | 5/2004 | Okano et al. |
| 2005/0255589 | A1* | 11/2005 | Reubinoff ............ C12N 5/0619 435/368 |
| 2009/0068742 | A1 | 3/2009 | Yamanaka |

FOREIGN PATENT DOCUMENTS

| JP | 2002291469 A | 10/2002 |
| WO | WO-2007069666 A1 | 6/2007 |

OTHER PUBLICATIONS

Meissner et al. (Aug. 2007) Direct reprogramming of genetically unmodified fibroblasts into pluripotent stem cells. Nature Biotechnology 25(10): 1177-1181.*
Okita et al. (Jul. 2007) Generation of germline-competent induced pluripotent stem cells. Nature 448: 313-318.*
Schopperle et al. (Nov. 2006) The TRA-1-60 and TRA-1-81 human pluripotent stem cell markers are expressed on podocalyxin in embryonal carcinoma. Stem Cells 25: 723-730.*
Plath et al. (Nature Reviews, 12: 253-265, 2011).*
Cyranoski, Nature, 516: 162-164, 2014.*
"Growth factor". Encyclopdia Britannica. Encyclopdia Britannica Online. Encyclopdia Britannica Inc., 2015. Web. Oct. 31, 2015 <http://www.britannica.com/science/growth-factor>.*
Conti et al., PLoS Biology, 3(9), e283: 1594-1606, Sep. 2005.*
Blelloch et al., Cell Stem Cell, 1(3): 245-247, Sep. 13, 2007.*
Kim et al., "Oct4-Induced Pluripotency in Adult Neural Stem Cells," *Cell* 136:411-419 (2009).
Liao et al., "Enhanced Efficiency of Generating Induced Pluripotent Stem (iPS) Cells from Human Somatic Cells by a Combination of Six Transcription Factors," *Cell Res.* 18:600-603 (2008) (Published online Apr. 15, 2008).
Nakagawa et al., "Generation of Induced Pluripotent Stem Cells Without Myc from Mouse and Human Fibroblasts," *Nat. Biotechnol.* 26:101-106 (2008).
Smukler et al., "Embryonic Stem Cells Assume a Primitive Neural Stem Cell Fate in the Absence of Extrinsic Influences," *J. Cell Biol.* 172:79-90 (2006).
Sridharan and Plath, "Illuminating the Black Box of Reprogramming," *Cell Stem Cell* 2:295-297 (2008).
Tropepe et al., "Direct Neural Fate Specification from Embryonic Stem Cells: A Primitive Mammalian Neural Stem Cell Stage Acquired through a Default Mechanism," *Neuron* 30:65-78 (2001).
Wernig et al., "Neurons Derived from Reprogrammed Fibroblasts Functionally Intergrate into the Fetal Brain and Improve Symptoms of Rats with Parkinson's Disease," *Proc. Natl. Acad. Sci. USA* 105:5856-5861 (2008).
Yu et al., "Induced Pluripotent Stem Cell Lines Derived from Human Somatic Cells," *Science* 318:1917-1920 (2007).
International Preliminary Report on Patentability for International Application No. PCT/JP2009/005856, mailed Dec. 7, 2010.
International Search Report for International Application No. PCT/JP2009/005856, dated Nov. 26, 2009 (date of completion of search) and Dec. 8, 2009 (date of mailing of report).
Aoi et al., "Generation of pluripotent stem cells from adult mouse liver and stomach cells," *Science* 321: 699-702 (2008).
Moon et al., "Induction of neural stem cell-like cells (NSCLCs) from mouse astrocytes by Bmi1," *Biochemical and Biophysical Research Communications* 371: 267-272 (2008).

(Continued)

*Primary Examiner* — Thaian N Ton
(74) *Attorney, Agent, or Firm* — Clark & Elbing LLP

(57) ABSTRACT

In order to provide a method for producing neural stem cells easily and quickly by inducing differentiation of somatic cells directly into neurospheres, dedifferentiation factors are introduced into somatic cells, which are then cultured in suspension in the presence of growth factors to produce the neurospheres, thereby allowing the neural stem cells to be produced quickly without establishing iPS cells.

13 Claims, 4 Drawing Sheets

(56) References Cited

OTHER PUBLICATIONS

Okada et al., "Spatiotemporal recapitulation of central nervous system development by murine embryonic stem cell-derived neural stem/progenitor cells," *Stem Cells* 26: 3086-3098 (2008).

Okano et al., "Transplantation of neural stem cells into the spinal cord after injury," *Seminars in Cell & Developmental Biology* 14: 191-198 (2003).

Takahashi and Yamanaka, "Induction of pluripotent stem cells from mouse embryonic and adult fibroblast cultures by defined factors," *Cell* 126: 663-676 (2006).

Takahashi et al., "Induction of pluripotent stem cells from fibroblast cultures," *Nature Protocols* 2: 3081-3089 (2007).

Zhou and Tripathi, "How to remake a fibroblast into a neural stem cell," *Cell Stem Cell* 10: 347-348 (2012).

Kumagai et al., "Roles of ES cell-derived gliogenic neural stem/progenitor cells in function recovery after spinal cord injury," PLoS One 4:e7706 (2009).

Tsuji et al., "Therapeutic potential of appropriately evaluated safe-induced pluripotent stem cells for spinal cord injury," Proc Natl Acad Sci U.S.A. 107:12704-12709 (2010).

* cited by examiner

A

B

A.

B.

METHOD FOR PRODUCING NEUROSPHERES

CROSS REFERENCE TO RELATED APPLICATIONS

This application is the U.S. national stage filing under 35 U.S.C. §371 of international application PCT/JP2009/005856, filed Nov. 4, 2009, which claims the benefit of U.S. Provisional Patent Application No. 61/198,365, filed Nov. 5, 2008.

TECHNICAL FIELD

The present invention relates to a method for producing neural stem cells.

BACKGROUND ART

Neural stem cells are useful as donor cells in transplant therapies for treating neurological disorders such as a spinal cord injury, and are anticipated for applications in regenerative medicine (Okano H, Ogawa Y, Nakamura M, kaneko S, Iwanami A, Toyama Y. (2003). "Transplantation of neural stem cells into the spinal cord after injury". Seminars in Cell & Developmental Biology 14(3): 191-198.). While it is known that the neural stem cells can be produced from embryonic stem cells (ES cells) (Okada Y, Matsumoto A, Shimazaki T, Enoki R, Koizumi A, Ishii S, Itoyama Y, Sobue G, Okano H. Stem Cells. 2008 Dec.;26(12):3086-98. Epub 2008 Aug. 28.), the use of human ES cells has been at issue from ethical viewpoints.

Recently, it became possible to produce induced pluripotent stem cells (iPS cells) having a pluripotency similar to the ES cells by selecting cells expressing Fbx15 gene among the cells which are obtained by introducing Oct3/4 gene, Sox2 gene, Klf4 gene and c-myc gene into somatic cells such as fibroblasts or hepatocytes and allowing them to grow (Takahashi K, Yamanaka S. (2006). "Induction of pluripotent stem cells from mouse embryonic and adult fibroblast cultures by defined factors.". Cell 126: 663-676; Takahashi K, Okita K, Nakagawa M, Yamanaka S. (2007). "Induction of pluripotent stem cells from fibroblast cultures". Nature Protocols 2: 3081-3089; Aoi T, Yae K, Nakagawa M, Ichisaka T, Okita K, Takahashi K, Chiba T, Yamanaka S. (2008). "Generation of pluripotent stem cells from adult mouse liver and stomach cells". Science 321(5889): 699-702; International Patent Publication WO2007/069666). The iPS cells have several advantages: for example, they are less ethically problematic because they can be established without using an embryo but rather with using somatic cells and rejection can be avoided when used in transplantation because they can be established from the cells of the recipient himself. Therefore, the neural stem cells produced by using the iPS cells would be more useful than the ES cells.

SUMMARY OF INVENTION

Technical Problem

However, establishment of iPS cells takes considerably long time, e.g. about one month for mouse, and three to four months for human. Therefore, it takes long time, e.g. more than half a year for human, to produce neural stem cells from fibroblasts via iPS cells. Thus, in consideration of applications in the regenerative medicine, development of methods for producing neural stem cells more easily and quickly has been anticipated.

Accordingly, the purpose of the present invention is to provide novel methods for producing neural stem cells easily and quickly, directly from somatic cells and without establishing iPS cells.

Solution to Problem

Through extensive effort to produce neural stem cells from fibroblasts, the inventors of the present application discovered that fibroblasts could be differentiated into neural stem cells in the form of neurospheres by introducing four dedifferentiation factors (Oct3/4, Sox2, Klf4 and c-Myc) into the fibroblasts and grow them for several days, then float-culturing the fibroblasts in the presence of growth factors. The present invention has thus been accomplished.

It should be noted that when the names of the factors such as "Sox2", "Oct3/4", "Klf4" and "c-Myc" are herein used by itself without a term like "gene" or "cDNA", they mean a protein as a gene product derived from these genes.

In one embodiment of the present invention, the method for producing a neural stem cell includes the steps of:
(i) introducing (a) dedifferentiation factor(s) into a somatic cell; and
(ii) float-culturing the dedifferentiation factor-introduced somatic cell in the presence of a growth factor to produce a neurosphere. The cell is cultured preferably for 2 to 14 days after the dedifferentiation factor(s) is/are introduced into the somatic cell. The dedifferentiation factors such as Sox2, Oct3/4 and Klf4, which may further include c-Myc, may be introduced into the somatic cell. The dedifferentiation factor-introduced somatic cell may be cultured in the presence of the growth factors such as LIF and FGF. Further, the dedifferentiation factor-introduced somatic cell may be cultured in the presence of cAMP, and preferably cultured in the absence of NAC (N-acetyl-L-cysteine). The somatic cell is preferably derived from a mammal, in particular mouse or human, preferably being derived from the skin or the liver, and more preferably being fibroblast or hepatocyte.

Advantageous Effects of Invention

According to the present invention, it has become possible to provide methods for producing neural stem cells quickly and directly from somatic cells without establishing iPS cells.

DESCRIPTION OF EMBODIMENTS

Figure 1:
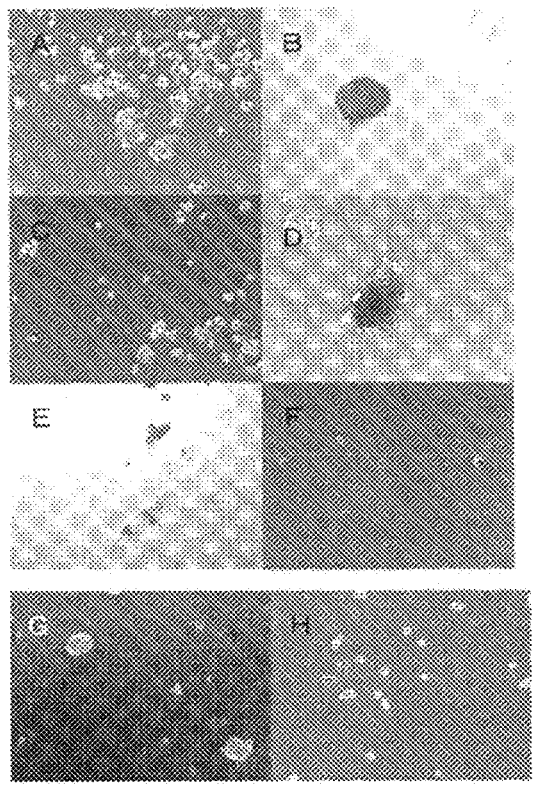
FIG. 1 shows the formation of neurospheres in the suspension culture of the dedifferentiation factor-introduced fibroblasts in one embodiment of the present invention.

Embodiments of the present invention accomplished based on the abovementioned discovery are hereinafter described in detail by giving examples. It should be noted that the present invention is not limited to these examples.

Where there is no particular explanations in embodiments or Examples, methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, New York (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., or their modified/changed methods are used. When using a commercial reagent kit and/or a measuring apparatus, protocols attached to them are used unless otherwise explained.

The object, characteristics, advantages of the present invention as well as the ideas thereof are apparent to those skilled in the art from the descriptions given herein, and the present invention can be easily worked by those skilled in the art based on the descriptions given herein. It is to be understood that the embodiments and specific examples of the invention described hereinbelow are to be taken as preferred examples of the present invention. These descriptions are presented only for illustrative or explanatory purposes and are not intended to limit the present inventions to these embodiments or examples. It is further apparent to those skilled in the art that various changes and modifications may be made based on the descriptions given herein within the intent and scope of the present invention disclosed herein.

—Introduction of Dedifferentiation Factors into Somatic Cells—

In order to produce neural stem cells from somatic cells, a dedifferentiation factor is introduced into the somatic cells at first.

The "somatic cell" as used herein represents a differentiated cell constituting an animal body excluding the cells in germ lines (such as egg cells, spermatids, oogonia, spermatogonia and their precursor cells) and the totipotent undifferentiated cells derived from embryos in early developmental stages (such as embryonic stem cells). The somatic cell is preferably derived from a mammal, and may be of any animal species such mouse or human. The animal may be either an adult, a fetus or an embryo. The somatic cell may be derived from an established cell line or primary cultured cells isolated from a tissue; preferably, it is in a normal state with regard to the chromosome number etc. The organ or tissue as a source of the somatic cell is not particularly limited, and includes skin, liver and blood. The characteristic of the somatic cell is not particularly limited as long as it has lost at least a part of the totipotency that a fertilized cell has, and the somatic cell includes fibroblast, epithelial cell, hepatocyte and blood cell. When the neural stem cells produced by the method according to the present invention are to be used for treatment of a patient, it is preferable to use the somatic cells which have been isolated from the patient himself.

While the dedifferentiation factors to be introduced into the somatic cells are not particularly limited, they may be the reprogramming factors that are used when producing the iPS cells. They preferably include a combination of gene products of the genes selected from each member of the gene families of Oct gene family, Klf gene family and Sox gene family. In view of the efficiency for producing neurospheres, more preferred is a combination further including a gene product of the gene from myc gene family. The genes belonging to the Oct gene family include Oct3/4, Oct1A and Oct6; the genes belonging to the Klf gene family include Klf1, Klf2, Klf4 and Klf5; and the genes belonging to the Sox gene family include Sox1, Sox2, Sox3, Sox7, Sox15, Sox17 and Sox18. The genes belonging to the myc gene family include c-myc, N-myc and L-myc. The gene product of the myc gene family may be substituted by a cytokine such as SCF and bFGF or a chemical compound such as azacitidine and sodium valproate(VPA).

The dedifferentiation factors other than the abovementioned combinations include a combination including Nanog gene and lin-28 gene etc. in addition to a gene from the Oct gene family and a gene from the Sox gene family. When introducing the factors into the cells, another type of gene product may be introduced in addition to the genes in the above-described combinations. Examples of the additional gene product include an immortalization-inducing factor such as TERT. It should be noted that if one or more of the abovementioned dedifferentiation factors is already expressed in the somatic cells to be used, introduction of such dedifferentiation factor(s) may be omitted. Also, if a chemical compound capable of substituting for the function of a particular dedifferentiation factor is present, it may be used in place of the dedifferentiation factor. The chemical compound includes Tranylcypromine, CHIR99021, SB431542, PD0325901, thiazovivin but is not limited thereto.

Since all of the genes encoding the above-mentioned dedifferentiation factors are highly conserved among the vertebrates, each of the genes herein referred to includes its homologues unless the name of a particular animal is indicated. Moreover, mutated genes including polymorphic genes are also encompassed as long as their products have a function comparable to that of the wild-type gene product.

The method for introducing these dedifferentiation factors into the somatic cells is not particularly limited; for example, the proteins of the dedifferentiation factors may be introduced by themselves (the protein transduction method), or alternatively, the DNAs encoding the dedifferentiation factors may be introduced to express in the somatic cells (the gene transfer technique).

The method for introducing the proteins of the dedifferentiation factors into the somatic cells is not particularly limited, and any method known to those skilled in the art may be employed. For example, a commercial product such as SAINT-Ph and Cellvader or a cationic lipid may be used for the introduction, and the proteins of the dedifferentiation factors may be introduced into the cells by fusing a peptide called Protein Transduction Domain (PTD) with the proteins and adding them to the culture medium.

Meanwhile, if the gene transduction method is to be employed for introducing the dedifferentiation factors into the somatic cells, a recombinant expression vector in which the DNA encoding the dedifferentiation factor is inserted downstream of an appropriate promoter for expression in the somatic cells may be constructed at first by any method known to those skilled in the art. Two or more kinds of the dedifferentiation factors may be inserted into a single vector. The expression vector to be used is not particularly limited, and examples include the pMX retrovirus vector etc. Then, the recombinant expression vectors constructed as above are introduced into the somatic cells. The method for the introduction may be any one of the methods known to those skilled in the art, such as the electroporation method, the calcium phosphate method, the lipofection method and methods utilizing retroviral infection. Thus, the dedifferentiation factors may be introduced into the somatic cells by introducing the expression vectors capable of expressing the dedifferentiation factors into the somatic cells and allowing the dedifferentiation factors to be expressed within the somatic cells.

The dedifferentiation factor-introduced somatic cells thus obtained are cultured under the same normal conditions as those for culturing the fibroblasts for a period of 2 to 14 days, preferably 3 to 10 days, and most preferably, 3 to 6 days in case of a mouse, or 7 to 10 days in case of a human. For example, the cells may be cultured using a DMEM medium containing 10% FBS in the presence of 5% $CO_2$ at 35 to 40° C., preferably at 37° C.

—Induction of Differentiation into Neurosphere of Dedifferentiation Factor-introduced Somatic Cell—

Next, by float-culturing the somatic cells treated as above in the presence of growth factors, their differentiation into neural stem cells in the form of neurospheres can be induced. The culture medium to be used is preferably a serum-free medium, such as DMEM: Ham F-12 medium (F-12) supplemented with glucose, glutamine, insulin, transferrin, progesterone, putrescine and selenium chloride. The growth factor to be added to the medium is not particularly limited as long as it is a factor or a combination of factors capable of inducing the differentiation of somatic cells into neurospheres, and is preferably FGF, LIF, B27, or a combination thereof. Preferable FGF is FGF-2 or FGF-8, and the concentration of FGF in the medium may be 5 to 50 ng/ml, preferably 10 to 40 ng/ml. The concentration of LIF in the medium is preferably about 1000 U/ml. B27 may be used in approximately 50-fold dilution by following the instruction manual from Invitrogen. The culturing is preferably conducted under the conditions of 5% $CO_2$ at 35 to 40° C., more preferably at 37° C. The efficiency for inducing the differentiation into neurosphere can be significantly improved by adding approximately 100 uM of cAMP to the medium. This is preferably conducted in the absence of N-acetyl-L-cysteine (NAC). The culture dish for the float culture is not particularly limited, but an uncoated plastic culture dish for bacterial culture is preferable.

By continuing under these conditions the culture of the dedifferentiation factor-introduced somatic cells with occasional exchanges of the culture medium, primary neurospheres start to be formed, generally in about 7 days in the cases of mouse fibroblasts and human fibroblasts. The medium may be appropriately exchanged, for example once in every 14 days. The period of the culture is not particularly limited as long as the neurospheres become ready to be recovered, and the mouse fibroblasts and the human fibroblasts usually become ready to be recovered in about 20 days. Note that the neurosphere obtained at first by inducing the somatic cell to differentiate as above is referred to as the primary neurosphere (PNS).

The primary neurosphere thus obtained may be dissociated and cultured to allow a secondary neurosphere to be formed again under the same conditions. This neurosphere formed again as well as the neurospheres formed by repeating the neurosphere dissociation-neurosphere formation processes are collectively referred to as the secondary neurospheres (SNSs).

Thus, by following the method according to the present invention, large amount of neurospheres can be formed from somatic cells in a short period of time.

—Induction of Differentiation from Neurosphere into Neuronal Cell—

The primary neurospheres and the secondary neurospheres thus obtained possess functions as the neural stem cells. For example, they can be differentiated into not only neurons but also glial cells (e.g. astrocytes, oligodendrocytes and Schwann cells) by culturing in a usual differentiation medium. In this case, a preferable medium for the induction of differentiation is the DMEM: Ham F-12 medium supplemented with glucose, glutamine, insulin, transferrin, progesterone, putrescine and selenium chloride (i.e. the medium for proliferating neural stem cells with omissions of FGF and heparin). Sonic hedgehog protein may be either present or absent. The culturing is preferably conducted under the conditions of 5% $CO_2$ at 35 to 40° C. for 5 to 7 days.

On the other hand, in the cases where ES cells are used to form embryoid bodies (EBs) in advance and then the EBs are induced to differentiate into neural stem cells, if a secondary neurosphere is cultured in a normal differentiation medium, not only neurons but also glial cell are differentiated, whereas if a primary neurosphere is cultured under the same culturing conditions, differentiation into only the neurons including motor neurons and GABAergic neurons is induced (Japanese Patent Publication No. 2002-291469).

Thus, by following the method according to the present invention, not only the neural stem cells can be differentiated from the somatic cells in a short period of time, but also the glial cells can be differentiated from the stage of the primary neurosphere.

EXAMPLES

Example 1

This example shows that the method for producing neural stem cells according to the present invention can induce the differentiation from the fibroblast into the neural stem cell.

—Preparation of Mouse Primary Fibroblasts—

In order to establish fibroblasts derived from the skin of a mouse, hair of an adult mouse (8 weeks, ICR mouse, male) was removed after cervical dislocation and an abdominal skin was collected. The isolated skin was washed four times in a phosphate-buffered saline (PBS) containing penicillin/streptomycin (50 U, 50 mg/ml) and 0.6% glutamine, and dermis was removed from the isolated skin. The dermis was placed on a cell culture dish, overlaid by a coverslip, and cultured in Primary Cell Starting Medium (TOYOBO).

On 6 to 7 days after the start of the culturing, the fibroblasts attached to the plastic dishes and the coverslips were detached by washing with 0.25% trypsin-EDTA, seeded on new plastic dishes at 50000 cells/ml, and cultured in the Primary Cell Starting Medium under the conditions of 37° C. and 5% $CO_2$ for 10 to 14 days.

—Preparation of Human Primary Fibroblasts—

From dermis collected from a human skin tissue, fibroblasts were obtained by the same method as used for the mouse with using DMEM containing 10% FBS under the conditions of 37° C. and 5% $CO_2$. Fibroblasts grown from a piece of the tissue were seeded by a trypsin treatment and grown as the primary fibroblasts. Then, in order to improve the efficiency of infection by a retrovirus, the primary fibroblasts were induced to express Slc7a1, a receptor for a retrovirus, by infecting them with Slc7a1-expressing lentiviruses (Takahashi and Yamanaka, Cell 2006 vol.126 p.663-676) overnight and allowing them to grow, and the resulting fibroblasts were used in the following experiments.

—Introduction of Dedifferentiation Factors into Established Fibroblasts—

The recombinant expression vectors of pMXs-Oct3/4, pMXs-Sox2, pMXs-Klf4 and pMXs-c-Myc (all from Addgen) containing each of the respective dedifferentiation factor DNAs were used to prepare the media containing retroviruses expressing either combination of four factors (Oct3/4, Sox2, Klf4 and c-Myc), three factors (Oct3/4, Sox2 and Klf4) or three factors (Oct3/4, Sox2 and c-Myc), whereas the pMX-GFP (Cell Biolabs Inc.) was used to prepare the medium containing GFP as an indicator for transformation and a negative control group against the factor-inserted groups, in the following manner. The method for preparing the vectors is described in detail in Takahashi and Yamanaka, Cell 2006 vol.126 p.663-676, which is incorporated herein by reference.

Platinum-E Retroviral Packaging Cells were grown in DMEM containing 10% FBS at 37° C. for 14 days prior to the packaging of the recombinant expression vectors. The respective mixtures of the recombinant expression vectors were transfected into the Platinum-E cells and the culture media were exchanged after 24 hours. The cells were further grown in DMEM containing 10% FBS under the conditions of 5% $CO_2$ and 35 to 40° C. for 24 hours and then the culture supernatants were recovered. Depending on the recombinant expression vectors used for the packaging, each of the recovered culture supernatants contains either one of the mixture of retroviruses expressing each of the four factors (Oct3/4, Sox2, Klf4 and c-Myc), the mixture of retroviruses expressing each of the three factors (Oct3/4, Sox2 and Klf4) without c-Myc, the mixture of retroviruses expressing each of the three factors (Oct3/4, Sox2 and c-Myc) without Klf4, or the retrovirus expressing GFP.

The culture supernatants thus obtained were added in appropriate amounts into the culture media of the primary fibroblasts to infect them with the retroviruses so as to allow expressions of either the four factors, the three factors or the GFP in the mouse primary fibroblasts, and expressions of either the four factors or the GFP in the human primary fibroblasts.

These retrovirus-transfected fibroblasts were seeded on plastic culture dishes and grown in DMEM containing 10% FBS under the conditions of 5% $CO_2$ and 35 to 40° C. for 24 hours for 5 days.

—Induction of Differentiation into Neurosphere—

The dedifferentiation factor-introduced fibroblasts cultured as above were dissociated by washing with 0.25% trypsin EDTA, resuspended in 10 ml of DMEM/F-12 serum-free medium (1:1, Invitrogen; containing 0.6% D-glucose, 5 mM HEPES, 3 mM $NaHCO_3$, 2 mM glutamine, 25 ug/ml insulin, 100 ug/ml transferrin, 20 nM progesterone, 60 uM putrescine and 30 nM sodium selenate) supplemented with LIF (recombinant human LIF; Chemi-Con, 100 U/ml) and FGF (PeproTech, 20 ng/ml) at the density of 50 cells/ul, seeded in bacterial plastic culture dishes, and cultured in suspension under the conditions of 37° C. and 5% $CO_2$ with exchanging the culture media every 14 days. On Day 3 and Day 20 during the suspension culture, the states of the cells were observed.

FIG. 1 shows the formation of the neurospheres as clusters of the dedifferentiation factor-introduced fibroblasts on Day 3 (A, C, E) and Day 20 (B, D, F) from the mouse cells to which either the 4 dedifferentiation factors (Oct3/4, Sox2, Klf4, c-Myc) had been introduced (A, B), the three dedifferentiation factors without c-Myc had been introduced (C, D), or GFP had been introduced (E, F). As shown in FIG. 1, whether the introduced dedifferentiation factors were the three factors without c-Myc or all the four factors, neurospheres could be obtained after the suspension culture of the fibroblasts.

FIG. 1 also shows the formation of the neurospheres on Day 3 during the suspension culture of the dedifferentiation factor-introduced fibroblasts from the human cells to which either all the four dedifferentiation factors (Oct3/4, Sox2, Klf4 and c-Myc) had been introduced (G) or the GFP had been introduced (H). As shown in FIG. 1, even when human cells were used, neurospheres could be obtained after the suspension culture of the fibroblasts.

Figure 2:
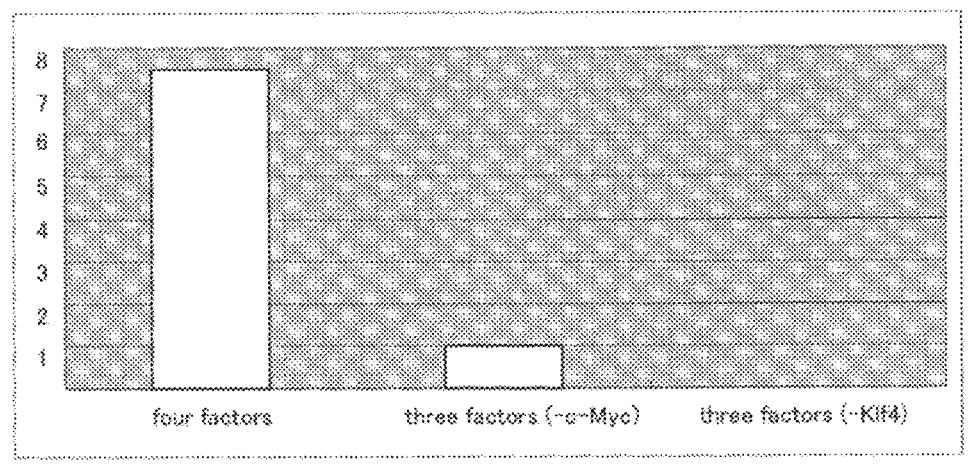
FIG. 2 is a graph showing a correlation between the kind of dedifferentiation factors to be introduced during a step of reprogramming the fibroblasts and the number of neurospheres formed after culturing the dedifferentiation factor-introduced fibroblasts in one embodiment of the present invention.

FIG. 2 shows the results obtained by counting of the number of the neurospheres produced under the respective conditions where the mouse cells were used. The fibroblasts to which the four factors had been introduced yielded 7.5 neurospheres on average per 10 ml of the culture medium and the fibroblasts to which the three factors without c-Myc had been introduced yielded 1 neurosphere on average, whereas the fibroblasts to which the three factors without Klf4 had been introduced or the GFP had been introduced did not yield a neurosphere. It should be noted that among the clusters of the cells having spherical shape, those with the diameter of 50 uM or more were counted in the measurements.

To summarize, in accordance with the method of the present invention, the neurospheres can be produced directly from the somatic cells without establishing iPS cells.

—Induction of Differentiation of Neurosphere—

Next, it will be shown that neurospheres thus obtained possess the potency as neural stem cells.

Neurospheres formed on Day 14 or later of the suspension culture (diameter>75 uM) were transferred one by one onto slides having chambers double-coated by Poly-O and fibronectin, and attached-cultured in 0.5 ml of DMEM/F-12 serum-free medium (1:1, Invitrogen; containing 0.6% D-glucose, 5 mM HEPS, 3 mM $NaHCO_3$, 2 mM glutamine, 25 ug/ml insulin, 100 ug/ml transferrin, 20 nM progesterone, 60 uM putrescine and 30 nM sodium selenate) supplemented with 2% FBS under the conditions of 37° C. and 5% $CO_2$ for 7 days. Resulting differentiated cells were fixed with 4% paraformaldehyde for 15minutes. After washing with PBS, the differentiated cells were treated with an anti-human betaIII-tubulin monoclonal antibody (Cat.No.T8660, Sigma, 1000-fold dilution), a rabbit anti-glial fibrillary acidic protein (GFAP) polyclonal antibody (Cat.No.Z0334, DAKO, 400-fold dilution), or anti-O4 (oligodendrocyte) monoclonal antibody (Cat.No.MAB345, Chemicon, 1000-fold dilution) at 4° C. overnight. Here, betaIII-tubulin was used as a marker for neurons, GFAP as a marker for astrocytes, and O4 as a marker for oligodendrocytes. Then, either of Alexa 488-labeled anti-mouse IgG goat antibody (Invitrogen, 500-fold dilution), Alexa 350-labeled anti-rabbit IgG goat antibody (Invitrogen, 500-fold dilution) or Alexa 555-labeled anti-mouse IgM goat antibody (Invitrogen, 1000-fold dilution) was appropriately used as the secondary antibodies, and the, specimens were observed under a fluorescence microscope.

Figure 3:
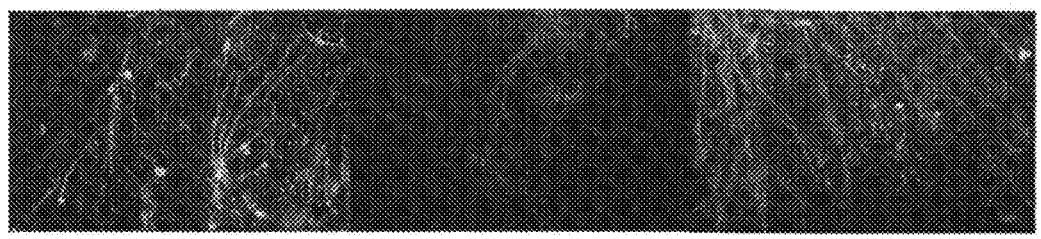
FIG. 3A shows localizations of neurons (visualized by green fluorescence), astrocytes (visualized by blue fluorescence) and oligodendrocytes (visualized by red fluorescence) among the neurospheres whose differentiation was induced in one embodiment of the present invention. Three instances are shown in this figure.
FIG. 3B is a graph showing the ratios of cell-types differentiated from the neurospheres derived directly from fibroblasts and those derived from iPS cells in one embodiment of the present invention.
Figure 3:
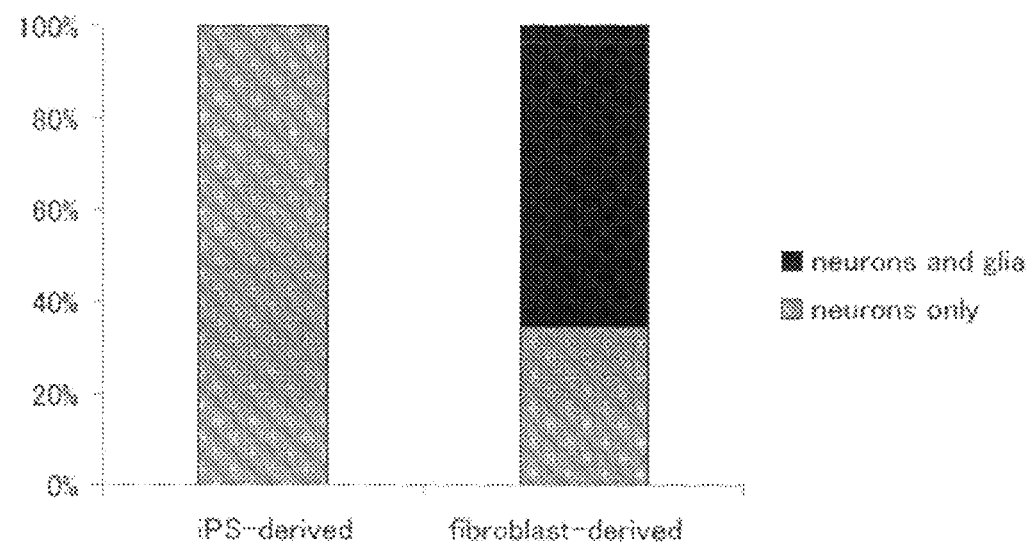

As shown in FIG. 3A, the attached-cultured cells were differentiated into neurons, astrocytes or oligodendrocytes, and thus it was confirmed that the obtained neurospheres possess the potency of differentiation into neuronal cells as well as glial cells.

Next, the potency to generate multiple differentiated cell-types was compared between the neurospheres derived directly from fibroblasts and those derived from iPS cells (38C2). The neurospheres derived directly from fibroblasts were allowed to differentiate as described above. On the other hand, 38C2 cells (Okita et al., Nature vol.448, pp.313-317, 2007) were allowed to form embryoid bodies (EBs) in the presence of $10^{-8}$ M retinoic acid and then cultured in a serum-free medium supplemented with 20 ng/ml FGF-2 (Okada et al., Dev. Biol. vol.275, pp.124-142, 2004). The EBs formed primary neurospheres in seven days in the culture, which were allowed to differentiate in the same way as those derived directly from fibroblasts. The differentiated cells were observed under the microscope and counted with identification of their cell-types. FIG. 3B shows the percentages of each of the differentiated neuronal cells and glial cells. As shown in the FIG. 3B, only neuronal cells were differentiated in all of the primary neurospheres derived from iPS cells (11 neurospheres), while neuronal cells as well as glial cells were differentiated in 65% of the neurospheres derived directly from fibroblasts (17 neurospheres out of 26 neurospheres).

Accordingly, the primary neurospheres obtained by the method of the present invention possess the potency for differentiation into glial cells and thus they are useful by themselves as the source for transplantation.

It should be noted that neurospheres could be produced by the method of the present invention also from the fibroblasts collected from the skin of a mouse embryo at almost the same efficiency.

Example 2

This example shows that the efficiency for inducing differentiation into neurospheres can be significantly improved by culturing the dedifferentiation factor-introduced fibroblasts in the presence of cAMP in the method for producing neural stem cells described in Example 1.

In order to examine the improvement of the efficiency for the induction of differentiation into neurospheres by cell death inhibitors of N-acetyl-L-cysteine (NAC) and 8-chlorophenylthio (pCPT-cAMP), a membrane-permeable analog of cAMP, media supplemented with either or both of 1 mM of NAC(Sigma) and 100 uM of pCPT-cAMP (Sigma) were used in the suspension culture as described in Example 1. Other procedures were followed in the same way as described in Example 1, and numbers of neurospheres on Day 20 of the culture were counted.

Figure 4:
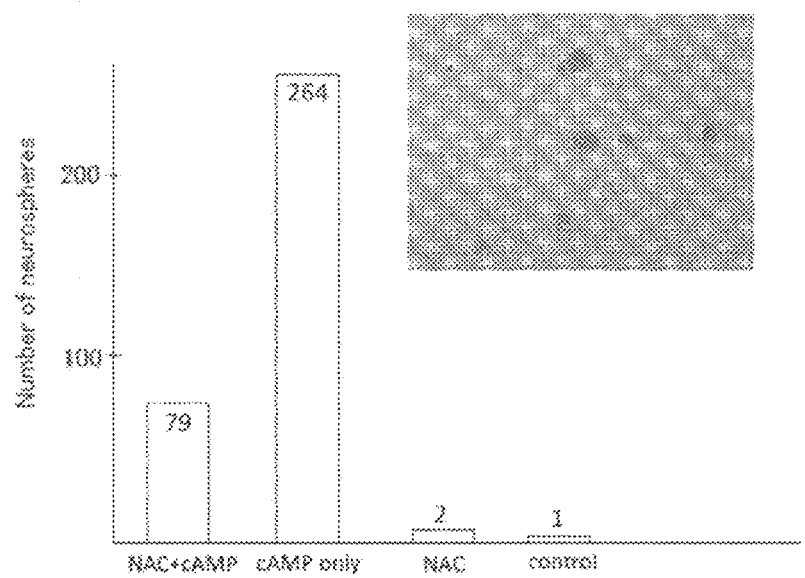
FIG. 4 is a graph showing (A) the effects of pCRT-cAMP (referred to as cAMP in the figure) and NAC on the numbers of the mouse neurospheres formed and (B) the effects of LIF, cAMP and Y27632 on the numbers of the human neurospheres formed, in one embodiment of the present invention. The pictures on the upper right-hand side are micrographs from observation of the neurospheres during the measurement.
Figure 4:
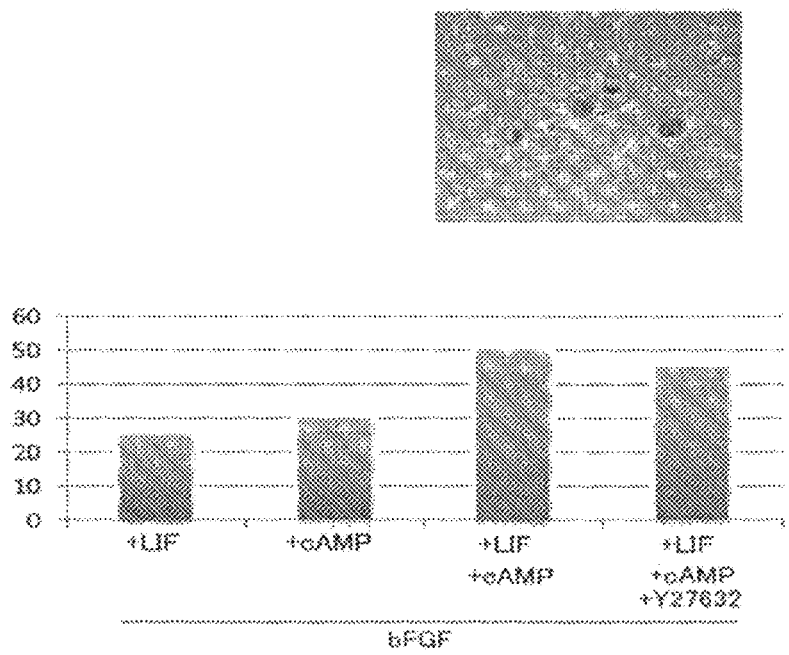

As shown in FIG. 4A, when only pCPT-cAMP was added, the number of neurospheres per 10 ml of the medium increased by over 100-fold as compared to the case where neither of the cell death inhibitors was added (Control Group). On the other hand, when only NAC was added, no difference was observed as compared to the Control Group. In the group where both NAC and pCPT-cAMP were added, the number of the obtained neurospheres considerably decreased as compared to the case where only pCPT-cAMP was added. Thus, NAC inhibited the effect of pCPT-cAMP's improving the efficiency for the induction of differentiation.

Accordingly, when the differentiation into neurospheres is induced by culturing the dedifferentiation factor-introduced fibroblasts, the differentiation-inducing efficiency will be significantly increased if cAMP is present. The induction is preferably carried out in the absence of NAC.

It should be noted that when fibroblasts obtained from the skin of a mouse embryo were used, the similar effect of cAMP was exerted by using the method of the present invention.

In the case of human fibroblasts, the culture media were supplemented with cAMP in place of or in addition to LIF or with cAMP, LIF and a ROCK inhibitor Y27632, and the number of the neurospheres obtained from 250000 cells was counted. As shown in FIG. 4B, LIF and cAMP had an additive effect but Y27632 had no effect on neurosphere formation.

Example 3

In this example, neurospheres were generated using embryos and adults of transgenic mice carrying an Oct4-GFP transgene and their differentiation stages were examined on the basis of expression of the Oct4 gene, which is expressed in undifferentiated cells.

Fibroblasts of adult mice were prepared according to the method in Example 1. Mouse embryonic fibroblasts were also prepared.

Figure 5:
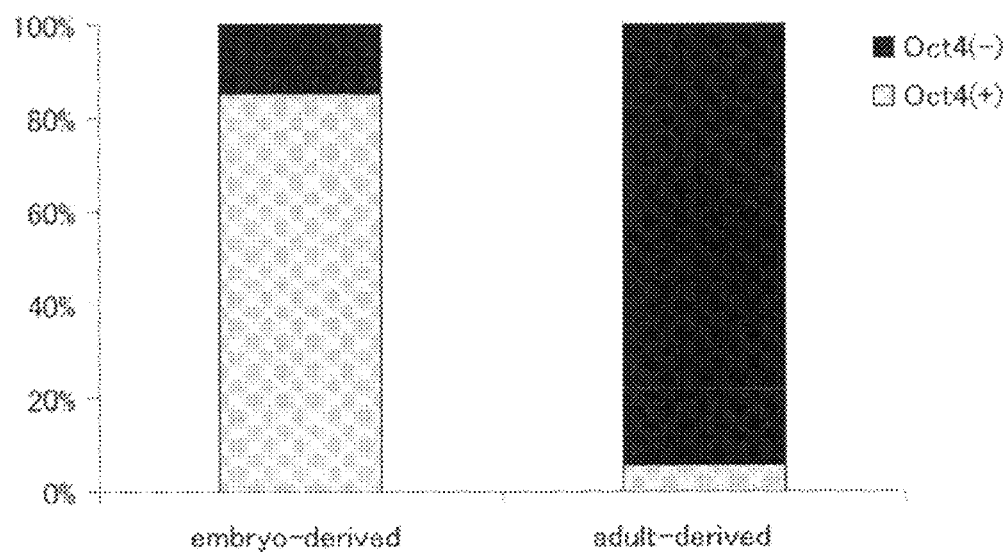
FIG. 5 is graphs showing the undifferentiated state of neurospheres indicated by Oct4 expression in one embodiment of the present invention.
Figure 5:
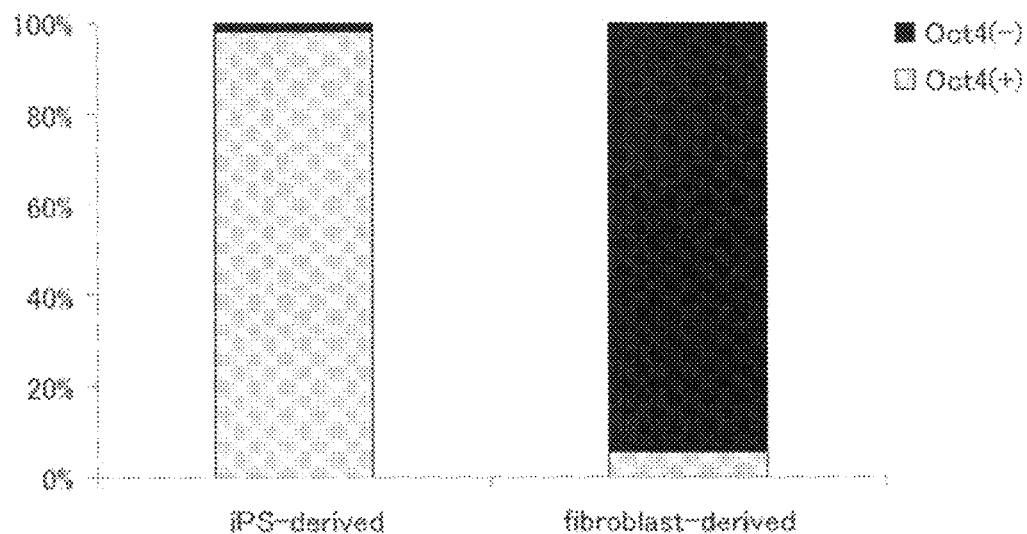

Then neurospheres were generated using the four factors (Oct3/4, Sox2, Klf4 and c-Myc) with these fibroblasts according to the method in Example 1. Under microscope, the numbers of neurospheres that contain a GFP-positive cell (GFP-positive neurospheres) and neurospheres that contain no GFP-positive cell (GFP-negative neurospheres) were counted. The ratios of GFP-positive neurospheres and GFP-negative neurospheres are shown in FIG. 5A.

85% (85 out of 100 neurospheres) and 6% (6 out of 100 neurospheres) of neurospheres derived from embryonic fibroblasts and from adult fibroblasts respectively were the GFP-positive neurospheres, indicating that the embryo-derived neurospheres were less differentiated than the adult-derived neurospheres. From the point of the tumorgenesis after transplantation, neurospheres at the more differentiated state is of less risk; thus, the adult-derived neurospheres are preferred to the embryo-derived neurospheres.

Similarly, the percentage of GFP-positive neurospheres in iPS-derived neurospheres was examined, compared with the adult-derived neurospheres. As shown in FIG. 5B, the GFP-positive neurospheres were 97% for the iPS-derived neurospheres, indicating that the iPS-derived neurospheres are even more undifferentiated. This fact suggests that the neurospheres produced according to the present invention has an advantage over the iPS-derived neurospheres in light of tumorgenesis after transplantation.

The invention claimed is:

1. A method for producing a mammalian neurosphere comprising the steps of:
  (i) introducing a vector or a set of vectors encoding the dedifferentiation factors Sox2, Oct3/4 and Klf4 into a mammalian fibroblast;
  (ii) culturing the dedifferentiation factor-introduced fibroblast for 2 to 14 days; and
  (iii) float-culturing the dedifferentiation factor-introduced fibroblast cultured in step (ii) in the presence of LIF and FGF2 to produce a mammalian neurosphere.

2. The method for producing a mammalian meurosphere according to claim 1, wherein c-Myc is further introduced into the mammalian fibroblast in step (i).

3. The method for producing a mammalian neurosphere according to claim 1, wherein the dedifferentiation factor-introduced fibroblast is cultured in the presence of cAMP in step (iii).

4. The method for producing a mammalian neurosphere according to claim 3, wherein the dedifferentiation factor-introduced fibroblast is cultured in the absence of N-acetyl-L-cysteine (NAC) in step (iii).

5. The method for producing a mammalian neurosphere according to claim 1, wherein the fibroblast is isolated from a mouse or a human.

6. The method for producing a mammalian neurosphere according to claim 5, wherein the fibroblast is isolated from skin.

7. The method for producing a mammalian neurosphere according to claim 1, wherein the dedifferentiation factor-introduced fibroblast is cultured for 3 to 10 days in step (ii).

8. The method for producing a mammalian neurosphere according to claim 1, wherein the dedifferentiation factor-introduced fibroblast is cultured for 3 to 6 days in the step (ii).

9. The method for producing a mammalian neurosphere according to claim 1, wherein the dedifferentiation factor-introduced fibroblast is cultured for 7 to 10 days in the step (ii).

10. The method for producing a mammalian neurosphere according to claim 1, wherein the dedifferentiation factor-introduced fibroblast is cultured for 24 hours to 5 days.

11. The method for producing a mammalian neurosphere according to claim 8, wherein the fibroblast is isolated from a mouse.

12. The method for producing a mammalian neurosphere according to claim 9, wherein the fibroblast is isolated from a human.

13. The method for producing a mammalian neurosphere according to claim 1, wherein the fibroblast is isolated from an adult.

\* \* \* \* \*